United States Patent [19]

Linhart et al.

[11] 4,207,243

[45] Jun. 10, 1980

[54] PREPARATION OF 2,5-DIMETHYLFURAN-3-CARBOXYLIC ACID ALKYL ESTERS

[75] Inventors: Friedrich Linhart, Heidelberg; Bjoern Girgensohn, Mannheim; Hans Merkle, Ludwigshafen; Hardo Siegel, Speyer; Hans-Richard Mueller, Bobenheim-Roxheim, all of Fed. Rep. of Germany

[73] Assignee: BASF Aktiengesellschaft, Fed. Rep. of Germany

[21] Appl. No.: 41,522

[22] Filed: May 22, 1979

[30] Foreign Application Priority Data

Jun. 14, 1978 [DE] Fed. Rep. of Germany ....... 2826013

[51] Int. Cl.$^2$ .................................................. C07D 307/68
[52] U.S. Cl. ................................................................ 260/347.5
[58] Field of Search ...................................... 260/347.5

[56] References Cited

U.S. PATENT DOCUMENTS

| | | | |
|---|---|---|---|
| 3,919,261 | 11/1975 | Merkle et al. | 260/347.5 |
| 4,054,585 | 10/1977 | Felauer et al. | 260/347.3 |

Primary Examiner—Richard Raymond
Attorney, Agent, or Firm—Keil & Witherspoon

[57] ABSTRACT

A process for the preparation of a 2,5-dimethylfuran-3-carboxylic acid ester from an α-acyloxypropionaldehyde and an acetoacetic acid ester in the presence of anhydrous iron-III chloride.

3 Claims, No Drawings

PREPARATION OF 2,5-DIMETHYLFURAN-3-CARBOXYLIC ACID ALKYL ESTERS

The present invention relates to a process for the preparation of a 2,5-dimethylfuran-3-carboxylic acid ester from an α-acyloxypropionaldehyde and an acetoacetic acid ester in the presence of anhydrous iron-III chloride.

2,5-Dimethylfuran-3-carboxylic acid alkyl esters are valuable intermediates for the preparation of crop protection agents. The preparation of 2,5-dimethylfuran-3-carboxylic acid alkyl esters by reaction of acetoacetic acid alkyl esters with α-acetoxypropionaldehyde has been disclosed in German Laid-Open Application DOS No. 2,207,098. This process takes place in two steps, successively requiring a basic catalyst and an acid catalyst, so that, in industrial operation, the reaction vessel must be changed in the course of the process because of the different sensitivities of reaction vessels to acid and basic reagents. Furthermore, the water formed in the reaction must be removed either by addition of a dehydrating agent or by azeotropic distillation.

It has also been disclosed, in German Laid-Open Application DOS No. 2,006,472, that similar furancarboxylic acids can be prepared by reacting an α-hydroxyketone with ethyl acetoacetate. This process has the disadvantage that the solvent used is benzene, which, because of its known toxicity, can only be used with strict safety precautions, and, secondly, 100 parts by weight of anhydrous zinc chloride are employed as the catalyst per 175 parts by weight of ethyl acetoacetate. Apart from the high cost of zinc chloride, environmental protection demands that such large amounts of this non-ferrous metal compound should not be introduced into the effluent.

We have found that a 2,5-dimethylfuran-3-carboxylic acid alkyl ester of the formula

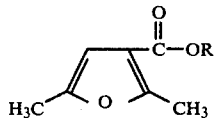

where R is lower alkyl of 1 to 4 carbon atoms, preferably ethyl or methyl, especially methyl, is obtained in a simple manner by reacting an α-acyloxypropionaldehyde of the formula

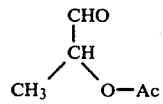

where Ac is acyl of 2 to 4 carbon atoms, preferably acetyl, with an acetoacetic acid ester of the formula

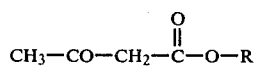

where R has the above meanings, at from +20° to +130° C., if the reaction is carried out in the presence of solid anhydrous iron-III chloride. Advantageously, solid anhydrous iron-III chloride and α-acetoxypropionaldehyde are added successively to a solution of the alkyl acetoacetate in the appropriate alcohol, during which addition the mixture becomes warm. The batch is then kept for some time at from 20° to 130° C., preferably from 40° to 90° C., especially from 50° to 80° C., and the ester which has separated out, for example after dilution with water, is then separated off; this last operation can be facilitated by adding a water-immiscible organic solvent, for example toluene, xylene, a higher alkyl-aromatic compound, a chloroaromatic compound, eg. chlorobenzene, an aliphatic hydrocarbon, eg. cyclohexane, hexane, heptane, octane, ligroin, or an aliphatic chlorohydrocarbon, eg. methylene chloride or dichloroethane. The crude product thus obtained is distilled.

By way of example, the weight ratio of iron-III chloride to acetoacetic acid ester may be from 0.25:1 to 1.5:1, the weight ratio of iron-III chloride to α-acetoxypropionaldehyde may be from 0.25:1 to 1.5:1, and the weight ratio of acetoacetic acid ester to α-acetoxypropionaldehyde may be from 0.5:1 to 1.5:1.

The water formed in, for example, the following reaction

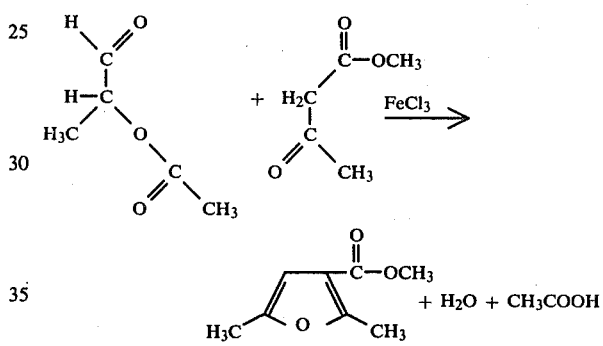

is bound by the iron-III choride, which at the same time serves as a catalyst, and is thereby abstracted from the reaction mixture. Anhydrous iron-III chloride can be handled in air without special precautionary measures or safety measures.

Since iron salts occur in most natural waters, for example chalybeatewater, and in tap water, as may be observed, for example, from the deposition of rust on bathtubs and other sanitary equipment, the introduction of iron-III chloride into the effluent presents absolutely no problems and may even be of advantage, since iron-III chloride is frequently added as a flocculating agent in sewage treatment plants.

The alcohols used as solvents are cheap and, since they are rapidly degraded biologically, can be introduced into the effluent without any misgivings; alternatively, however, they can be recovered. The acetic acid formed in the reaction is also rapidly decomposed by the bacteria of a sewage treatment plant.

The process according to the invention can be varied by distilling the reaction mixture instead of decomposing it with water; the distillation may be carried out under reduced pressure, either from the very start or when the desired ester is being distilled. In this way, the solvent can also be recovered; whilst the iron salts remaining in the reaction vessel can be removed with water.

The Examples which follow illustrate the advantages of the process according to the invention.

EXAMPLE 1

12.2 parts by weight of anhydrous iron-III chloride followed by 44.9 parts by weight of 85.5 percent strength by weight α-acetoxypropionaldehyde are added to a solution of 34.8 parts by weight of methyl acetoacetate in 36 parts by weight of methanol, during which addition the mixture rises to the boil. The mixture is then refluxed for a further 1–6 hours and, when it has cooled, is mixed with 80 parts by weight of water and 37.5 parts by weight of dichloroethane; the water phase is separated off and is extracted twice, each time with 25 parts by weight of dichloroethane. The dichloroethane is distilled off under atmospheric pressure and the product is then distilled under reduced pressure. 39 parts by weight of 2,5-dimethylfuran-3-carboxylic acid methyl ester of boiling point 92° C./26 mbar are obtained.

EXAMPLE 2

27 parts by weight of anhydrous iron-III chloride are added to a solution of 116 parts by weight of methyl acetoacetate in 120 parts by weight of methanol and thereafter 149 parts by weight of 85.5 percent strength α-acetoxypropionaldehyde are added dropwise, sufficiently slowly that the temperature does not rise above 37° C. The mixture is stirred overnight at room temperature (20° C.), is then boiled for 2 hours, and, when it has cooled, is worked up as described in Example 1. Distillation gives 116.6 parts by weight of 2,5-dimethylfuran-3-carboxylic acid methyl ester.

EXAMPLE 3

27 parts by weight of iron-III chloride and 149 parts by weight of 85.5 percent strength α-acetoxypropionaldehyde are added to a solution of 116 parts by weight of methyl acetoacetate in 120 parts by weight of methanol at a rate such that the mixture rises to the boil. The methanol is distilled off under atmospheric pressure and the product is then distilled under reduced pressure. 106.2 parts by weight of 2,5-dimethylfuran-3-carboxylic acid methyl ester, of boiling point 89° C./20 mbar, are obtained.

EXAMPLE 4

27 parts by weight of anhydrous iron-III chloride and 149 parts by weight of 85.5 percent strength α-acetoxypropionaldehyde are added to a solution of 130 parts by weight of ethyl acetoacetate in 120 parts by weight of ethanol, at a rate such that the mixture rises to 80° C. The ethanol is distilled off under atmospheric pressure. The 2,5-dimethylfuran-3-carboxylic acid ethyl ester is then distilled off at 96°–100° C./25 mbar.

EXAMPLE 5

40 parts by weight of iron-III chloride and 136 parts by weight of 85 percent strength α-acetoxypropionaldehyde are added successively to a solution of 150 parts by weight of methyl acetoacetate in 120 parts by weight of methanol. The mixture, which becomes warm, is then refluxed for 2 hours. When it has cooled, the reaction solution is washed with water and distilled. 127 g of 2,5-dimethylfuran-3-carboxylic acid methyl ester are obtained.

We claim:

1. A process for the preparation of a 2,5-dimethylfuran-3-carboxylic acid alkyl ester of the formula

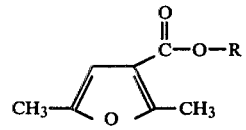

where R is lower alkyl, by reacting an α-acyloxypropionaldehyde of the formula

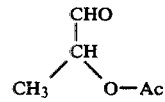

where Ac is acyl, with an acetoacetic acid ester of the formula

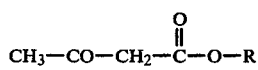

where R has the above meanings, at from +20° to +130° C., wherein the reaction is carried out in the presence of solid anhydrous iron-III chloride.

2. A process as claimed in claim 1 for the preparation of 2,5-dimethylfuran-3-carboxylic acid methyl ester, wherein methyl acetoacetate dissolved in methanol, and α-acetoxypropionaldehyde, are used as starting materials.

3. A process as claimed in claim 1 for the preparation of 2,5-dimethylfuran-3-carboxylic acid ethyl ester, wherein ethyl acetoacetate dissolved in ethanol, and α-acetoxypropionaldehyde, are used as starting materials.

* * * * *